United States Patent [19]

Fritsch et al.

[11] Patent Number: 5,445,827
[45] Date of Patent: Aug. 29, 1995

[54] EFFERVESCENT IBUPROFEN PREPARATIONS

[75] Inventors: Christian Fritsch, Odenthal; Werner Gräwingholt, Cologne, both of Germany

[73] Assignee: Bayer Aktiengesellschaft, Leverkusen, Germany

[21] Appl. No.: 88,472

[22] Filed: Jul. 7, 1993

Related U.S. Application Data

[63] Continuation of Ser. No. 876,704, Apr. 29, 1992, abandoned, which is a continuation of Ser. No. 431,585, Nov. 3, 1989, abandoned.

[30] Foreign Application Priority Data

Nov. 12, 1988 [DE] Germany .......................... 38 38 431.0

[51] Int. Cl.$^6$ ..................... A61K 9/46; A61K 9/20
[52] U.S. Cl. .................... 424/466; 424/465; 424/489
[58] Field of Search ............... 424/466, 501, 489, 465

[56] References Cited

U.S. PATENT DOCUMENTS

| | | | |
|---|---|---|---|
| 4,684,666 | 8/1987 | Haas | 514/557 |
| 4,689,218 | 8/1987 | Gazzaniga et al. | 424/43 |

FOREIGN PATENT DOCUMENTS

| | | |
|---|---|---|
| 0070714 | 7/1982 | European Pat. Off. . |
| 0203768 | 12/1986 | European Pat. Off. . |
| 0228164 | 7/1987 | European Pat. Off. . |
| 0369228 | 7/1987 | European Pat. Off. . |
| 0971700 | 2/1961 | United Kingdom . |

OTHER PUBLICATIONS

J. C. Johnson, "Tablet Manufacture," 1974, pp. 144–146.
James E. F. Reynolds, ed., *Martindale: The Extra Pharmacopoeia*, 1982, p. 256.

*Primary Examiner*—Thurman K. Page
*Assistant Examiner*—Sally Gardner
*Attorney, Agent, or Firm*—Sprung Horn Kramer & Woods

[57] ABSTRACT

An effervescent ibuprofen preparation comprising
a) basic granules consisting of 1 part by weight of water-soluble ibuprofen salt, 2 to 10 parts by weight of excipient, 0.3 to 0.8 part by weight of stabilizer and 0.1 to 1 part by weight of sodium carbonate or potassium carbonate and
b) 1 to 4 parts by weight of an acid component.

4 Claims, No Drawings

EFFERVESCENT IBUPROFEN PREPARATIONS

The instant application is a continuation of application Ser. No. 07/876,704, filed Apr. 29, 1992, now abandoned, which is a continuation of application Ser. No. 07/431,585, filed Nov. 3, 1989, now abandoned.

The invention relates to clear-dissolving effervescent ibuprofen preparations and a process for their preparation.

Ibuprofen is a medicament having an analgesic and inflammation-inhibiting effect, which irritates the gastric mucosa in a similar manner to acetylsalicylic acid and is relatively slowly absorbed. Moreover, the taste of ibuprofen is so bad that tablets are usually provided with a taste-masking coating. Since with acetylsalicylic acid the problems of irritation of the gastric mucosa and protracted absorption can be solved by administration in the form of effervescent tablets and granules, the use of this form of medicament was also taken into consideration for ibuprofen. However, in this connection it was shown that the use of customary effervescent mixtures is unsuccessful.

In spite of diverse efforts it was not possible to dissolve the extremely poorly soluble ibuprofen crystals from an effervescent preparation rapidly and completely in a glass of water, so that really unattractive administration forms always resulted.

EP-A 228,164 describes an effervescent preparation containing ibuprofen—or its salts—which contains ibuprofen in suspended form in a glass of water after effervescent reaction has taken place. This preparation has the disadvantage that the merits of an analgesic effervescent tablet, such as better gastric compatibility and more rapid onset of action, are not given from the start.

DE-A 3,638,414 describes the addition of arginine or lysine in an amount exceeding the molar amount in order to obtain a soluble form of ibuprofen. The effervescent composition contains sodium hydrogentartrate as the acid component. The addition of these components brings large disadvantages with it. Arginine and lysine are expensive for use as a pharmaceutical auxiliary and exceed the costs of the active compound ibuprofen. Sodium hydrogentartrate acts so weakly as an acid that, at a pH of above 6.5 for the total system, the intensity of the effervescent reaction leaves something to be desired and is almost no longer detectable at all. Thus a strong effervescent effect which is positively attractive to the patient is in practice not achieved.

EP-A 203,768 describes a therapeutic effervescent composition which can contain paracetamol, acetylsalicylic acid or ibuprofen. This invention proposes granulation of the active compound (for example ibuprofen) with a granulating auxiliary (for example PVP), mixing these granules with a part of a component of the effervescent mixture and then mixing this preliminary mixture with an effervescent system. The procedure described is suitable for the preparation of clearly soluble effervescent preparations of paracetamol and aspirin, but not of ibuprofen. In accordance with this invention, no effervescent preparations containing 200 mg of ibuprofen can be prepared which dissolve in 100 to 200 ml of water at 15° to 25° C. so rapidly and clearly that after 2 minutes more than 95% of the active compound is present in solution.

In the preparation of effervescent ibuprofen preparations by conventional procedures, the principal difficulty consists in that, at a pH value of the ready-dissolved preparation of 6.8 (7.2), which is necessary in order to keep 200 (400) mg of ibuprofen in solution, the effervescent reaction between the carbonate component and the acid component comes to a standstill.

If ibuprofen is employed in the acid form, the rate of dissolution is low, so that undissolved residues are still to be found in the glass of water after some time. The rate of dissolution can be increased if the sodium, potassium or ammonium salt of ibuprofen is employed. However, precipitates, which only go into solution again very slowly, then result through the direct contact of dissolved ibuprofen salt with the acid component of the effervescent mixture.

An effervescent preparation has now been found which eliminates all disadvantages previously mentioned and is suitable for the preparation of rapidly and clearly dissolving effervescent ibuprofen preparations. The effervescent preparation according to the invention has the following composition:

a) Basic granules consisting of 1 part by weight of water-soluble ibuprofen salt, 2 to 10 parts by weight, preferably 4 to 7 parts by weight, of excipient, 0.3 to 0.8 parts by weight, preferably 0.4 to 0.7 parts by weight, of stabilizer and 0.2 to 1 part by weight, preferably 0.4 to 0.7 parts by weight, of sodium carbonate or potassium carbonate.

b) Acid components 1 to 4 parts by weight, preferably 1.5 to 2.5 parts by weight, relative to 1 part by weight of water-soluble ibuprofen salt.

Sodium salts, potassium salts and ammonium salts of ibuprofen are preferably employed as water-soluble ibuprofen salts. The sodium and potassium salts of ibuprofen are particularly preferred.

Water-soluble salts of ibuprofen with amino acids, such as, for example, arginine, lysine or ornithine or with other pharmaceutically acceptable organic amino compounds such as, for example, N-methylglucosamine, piperazine, N-(2-hydroxyethyl)piperazine or tris(-hydroxymethyl)aminomethane are also suitable.

The water-soluble ibuprofen salts may contain ibuprofen as the racemate (R(−)-form and S(+)-form) or also only in the form of the pure S(+)-enantiomer or only in the form of the pure R(−)-enantiomer.

The effervescent preparation according to the invention offers a solution for the problems mentioned.

Surprisingly, it has been found that a clear-dissolving, clearly effervescing ibuprofen preparation can be prepared if ibuprofen is granulated in the form of its water-soluble salts, preferably sodium salts or potassium salts, together with the excipient and the stabilizer, and the granules are subsequently sprayed with a 5- to 20-percent, preferably 15- to 18-percent, solution of the carbonate and then dried. A suitable amount of the acid component is admixed to these basic granules.

The sodium salt of ibuprofen is particularly preferred for the preparation of the effervescent ibuprofen preparation.

Powders, granules or tablets can be prepared from the preparation, consisting of basic granules and acid components, according to the invention. Granules and tablets are preferred.

According to the invention, the excipient may be a water-soluble, non-effervescing component, such as, for example, sucrose, lactose, mannitol, monosodium citrate and trisodium citrate or an effervescing component such as, for example, sodium hydrogencarbonate or potassium hydrogencarbonate, sodium carbonate or potassium carbonate or mixtures of these components. Preferably, sodium hydrogencarbonate is employed.

The significance of the stabilizer in the invention is to keep ibuprofen in solution once dissolved and to prevent precipitates. For this purpose, water-soluble polymers such as, for example, polyvinyl alcohol, polyvinylpyrrolidone, polyvinylpyrrolidone/polyvinyl acetate copolymer, polyethylene glycol, polyethylene glycol/polypropylene glycol copolymer, preferably polyvinylpyrrolidone, polyvinylpyrrolidone/polyvinyl acetate copolymer and cellulose ethers, preferably hydroxypropylmethylcellulose, are suitable. Particularly preferably, polyvinylpyrrolidone is employed as the stabilizer.

The organic acids customary for effervescent preparations, such as, for example, citric acid, tartaric acid, succinic acid, maleic acid, malic acid, malonic acid, adipic acid, fumaric acid, ascorbic acid, monosodium citrate, disodium citrate, potassium hydrogentartrate or sodium hydrogenphosphate can be employed as the acid components. Preferably, citric acid or tartaric acid are employed.

The effervescent preparation may contain other additives such as binders, for example glycocoll, sweeteners, for example saccharin or cyclamate, flavorings, wetting agents, for example dioctyl sodium sulphosuccinate or sodium lauryl sulphate and antifoams, for example silicone oil.

The addition of a lubricant is necessary for the preparation of effervescent tablets from the effervescent granules.

If this lubricant is missing from the composition and the tabletting equipment is filled with powder constituents, the tablets obtained show a rough unsightly surface. The selection of a lubricant suitable for effervescent tablets generally turns out to be extremely difficult.

Water-insoluble lubricants such as, for example, magnesium stearate, stearic acid, talc, paraffin and hydrogenated castor oil render turbid the solution desired as clear. Polyethylene glycol, fumaric acid, adipic acid, sodium benzoate and sodium stearyl fumarate are suitable as more or less readily water-soluble, but mostly not very effective lubricants.

Polyethylene glycol only possesses insufficient lubricant properties and prolongs the dissolution behavior of effervescent tablets considerably. Moreover, the substance reduces the internal hardness of the tablets.

Fumaric acid and adipic acid have to be added in relatively high concentrations (10 to 15%). In effervescent ibuprofen tablets, due to their acidic character, they precipitate the active compound in its poorly soluble acid form, as a result of which unsightly turbidity results. At the same time, both lubricants reduce the hardness of the tablets.

Sodium stearyl fumarate is only soluble in water up to about 1%. Therefore not more than 3% of this substance can be employed, for example, in a 3 g effervescent tablet. In this amount, the action as a lubricant frequently does not suffice.

Sodium benzoate has to be declared as an active ingredient and is in this respect not suitable.

It has been found that pharmaceutically acceptable salts of fumaric acid and adipic acid, such as the sodium, potassium, ammonium, calcium and magnesium salts, preferably the sodium or potassium salts, are particularly suitable in a concentration of 3 to 10%, preferably 5 to 8%, relative to the total preparation, as lubricants for the preparation of effervescent ibuprofen tablets. These lubricants are in general admixed to the effervescent preparation, consisting of basic granules and acid components, as fine powders having a particle size of less than 50, preferably less than 20, micrometers. Similarly, it is possible to spray the lubricants onto the basic granules from an aqueous solution and then to admix the acid component.

Disodium fumarate is particularly preferred as the lubricant.

The invention is intended to be illustrated by the following examples.

EXAMPLE 1

Effervescent ibuprofen granules, of which 200 mg of ibuprofen are to be administered, are composed as follows:

| Ibuprofen sodium salt | 221.3 mg |
| Polyvinylpyrrolidone | 120.0 mg |
| Sodium hydrogencarbonate | 1,363.7 mg |
| Sodium carbonate | 100.0 mg |
| Citric acid | 395.0 mg |

136.37 kg of sodium hydrogencarbonate are weighed into the container of a fluidized bed granulator. 22.13 kg of ibuprofen sodium salt, 12.0 kg of polyvinylpyrrolidone and 80 kg of water are weighed into a stirring vessel and stirred until a clear solution results. The solution is sprayed onto the sodium hydrogencarbonate at a hot air temperature of about 100° C., whereupon granules result. A solution of 10 kg of sodium carbonate in 50 kg of water is then sprayed onto these granules. The basic granules coated in this way with a layer of sodium carbonate are then dried.

39.5 kg of citric acid are admixed to the basic granules in order thus to obtain the ready effervescent ibuprofen granules.

Packaging can be carried out in aluminum sachets in single amounts of 2.2 g. The granules contained in a sachet when dissolved in 100 ml of water give a clear ibuprofen solution having a pH of 6.7 after one minute.

EXAMPLE 2

In accordance with the preparation procedure as in Example 1, basic granules having the following composition are prepared:

| Ibuprofen sodium salt | 22.13 mg |
| Polyvinylpyrrolidone | 8.00 mg |
| Sodium hydrogencarbonate | 135.00 mg |
| Sodium carbonate | 15.00 mg |

180.13 kg of these granules are sprayed with a solution of 15 kg of disodium fumarate in 100 kg of water in a fluidized bed apparatus and subsequently dried. The granules pretreated in this way are mixed with 54.87 kg of citric acid and subsequently pressed to give effervescent tablets having an individual weight of 2.5 g. The tablets have a dissolution time of 2 minutes in 100 ml of water and in the course of this give a clear solution having a pH of 6.8.

It is understood that the specification and examples are illustrative but not limitative of the present invention and that other embodiments within the spirit and scope of the invention will suggest themselves to those skilled in the art.

We claim:

1. An effervescent ibuprofen preparation comprising a) basic granules consisting essentially of 1 part by weight of ibuprofen sodium salt; 6.1 parts by weight of sodium hydrogen-carbonate; 0.54 parts by weight of polyvinylpyrrolidone; 0.45 parts by weight of sodium carbonate; and
b) 1.79 parts by weight of citric acid; about 2.2 parts of said preparation in 100 parts of water in about 1 minute forming a clear solution of about pH 6.7.

2. An effervescent ibuprofen preparation according to claim 1, in the form of tablets or granules.

3. Effervescent ibuprofen tablets according to claim 2, additionally containing a lubricant.

4. Effervescent ibuprofen tablets according to claim 3, wherein the lubricant is the sodium salt or potassium salt of fumaric acid or adipic acid.

* * * * *